United States Patent
Yamane et al.

(10) Patent No.: US 12,193,779 B2
(45) Date of Patent: Jan. 14, 2025

(54) CAMERA DRAPE

(71) Applicant: Meilleur Co., Ltd., Chiba (JP)

(72) Inventors: Tsurashi Yamane, Chiba (JP); Kaori Nakagawa, Chiba (JP); Junko Ochibe, Chiba (JP)

(73) Assignee: Meilleur Co., Ltd., Chiba (JP)

( * ) Notice: Subject to any disclaimer, the term of this patent is extended or adjusted under 35 U.S.C. 154(b) by 0 days.

(21) Appl. No.: 17/607,531

(22) PCT Filed: Apr. 20, 2021

(86) PCT No.: PCT/JP2021/016001
§ 371 (c)(1),
(2) Date: Apr. 13, 2022

(87) PCT Pub. No.: WO2022/172477
PCT Pub. Date: Aug. 18, 2022

(65) Prior Publication Data
US 2022/0331040 A1   Oct. 20, 2022

(30) Foreign Application Priority Data
Feb. 10, 2021  (WO) .................. PCT/JP2021/004870

(51) Int. Cl.
*A61B 1/00*   (2006.01)
*A61B 1/04*   (2006.01)
*A61B 46/10*  (2016.01)

(52) U.S. Cl.
CPC .......... *A61B 46/10* (2016.02); *A61B 1/00135* (2013.01); *A61B 1/0014* (2013.01);
(Continued)

(58) Field of Classification Search
None
See application file for complete search history.

(56) References Cited

U.S. PATENT DOCUMENTS 4,522,196 A   6/1985  Cunningham
5,274,500 A   12/1993 Dunn
(Continued)

FOREIGN PATENT DOCUMENTS

| | | |
|---|---|---|
| GB | 2483154 A | 2/2012 |
| JP | 2017074372 A | 4/2017 |
| JP | 2020151403 A | 9/2020 |

OTHER PUBLICATIONS

International Search Report and Written Opinion related to PCT/JP2021/016001 reported on Jun. 22, 2021.
(Continued)

*Primary Examiner* — Timothy J Neal
(74) *Attorney, Agent, or Firm* — von Briesen & Roper, s.c.

(57) ABSTRACT

Provided is a camera drape which enables easy replacement of a rigid endoscope during a surgical operation while suppressing deterioration in the quality of video. A camera drape comprises: a spacer that is arranged between an endoscope-side lens of a rigid endoscope and a camera-side lens of a camera head; and a drape body that is attached to the spacer and covers, among the rigid endoscope and the camera head, only the camera head. The spacer includes a clamping plate having a through hole that faces the endoscope-side lens and the camera-side lens in a state where the spacer is clamped between an eyepiece unit for supporting the endoscope-side lens and an endoscope connection unit for supporting the camera-side lens.

4 Claims, 4 Drawing Sheets

(52) U.S. Cl.
CPC ...... *A61B 1/00142* (2013.01); *A61B 1/00163* (2013.01); *A61B 1/04* (2013.01); *A61B 2562/247* (2013.01)

(56) References Cited

U.S. PATENT DOCUMENTS

| | | | |
|---|---|---|---|
| 5,433,221 A | | 7/1995 | Adair |
| 5,792,045 A | * | 8/1998 | Adair ................ A61B 1/00128 |
| | | | 600/125 |
| 5,876,328 A | * | 3/1999 | Fox ..................... A61B 46/10 |
| | | | 600/122 |
| 5,882,295 A | * | 3/1999 | Kope ................... A61B 46/10 |
| | | | 600/122 |
| 2018/0256274 A1 | | 9/2018 | Baba |
| 2020/0297185 A1 | | 9/2020 | Michihata |

OTHER PUBLICATIONS

European Search Report related to Application No. 21791236.9 reported on May 12, 2022.

\* cited by examiner

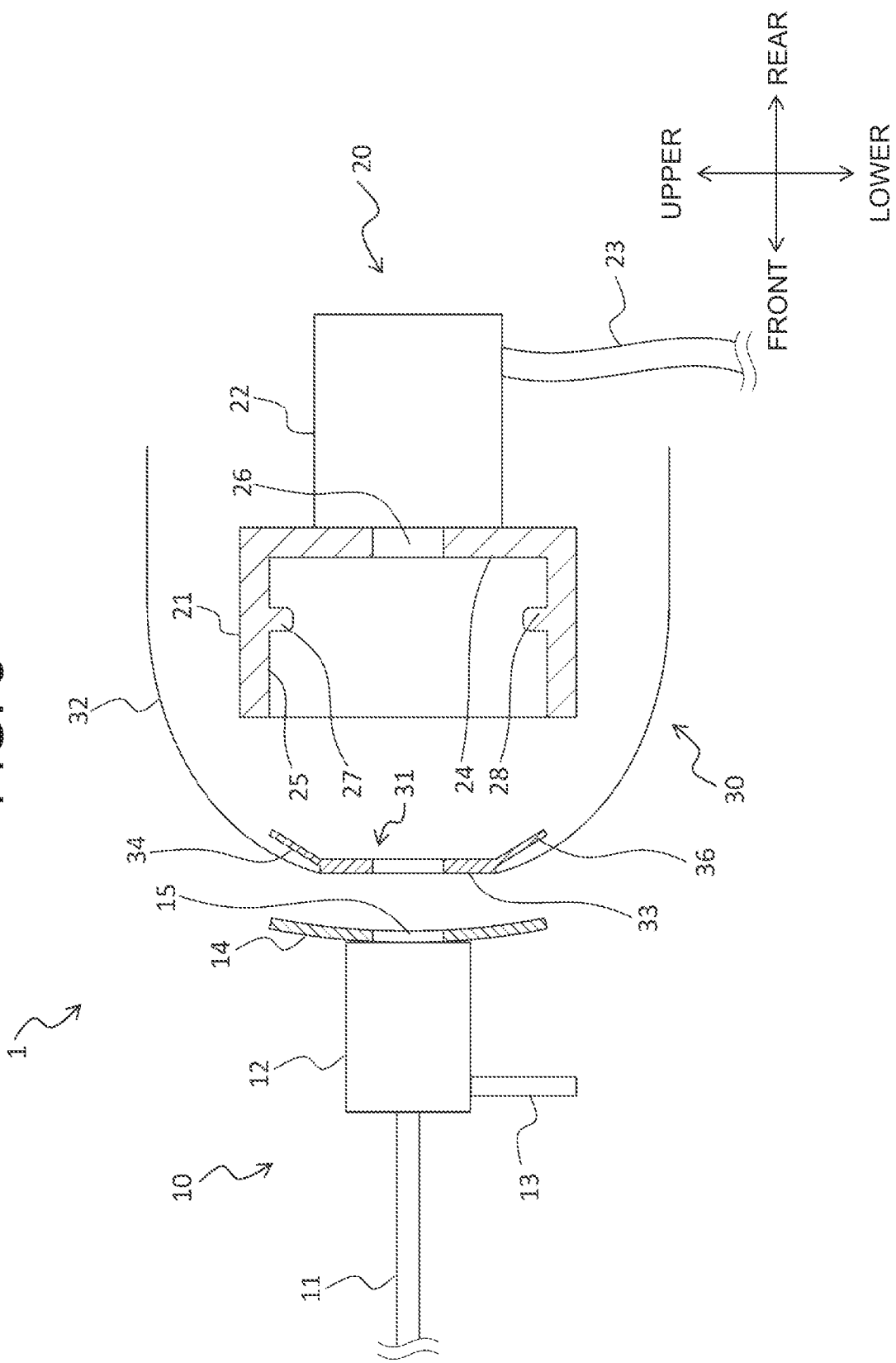

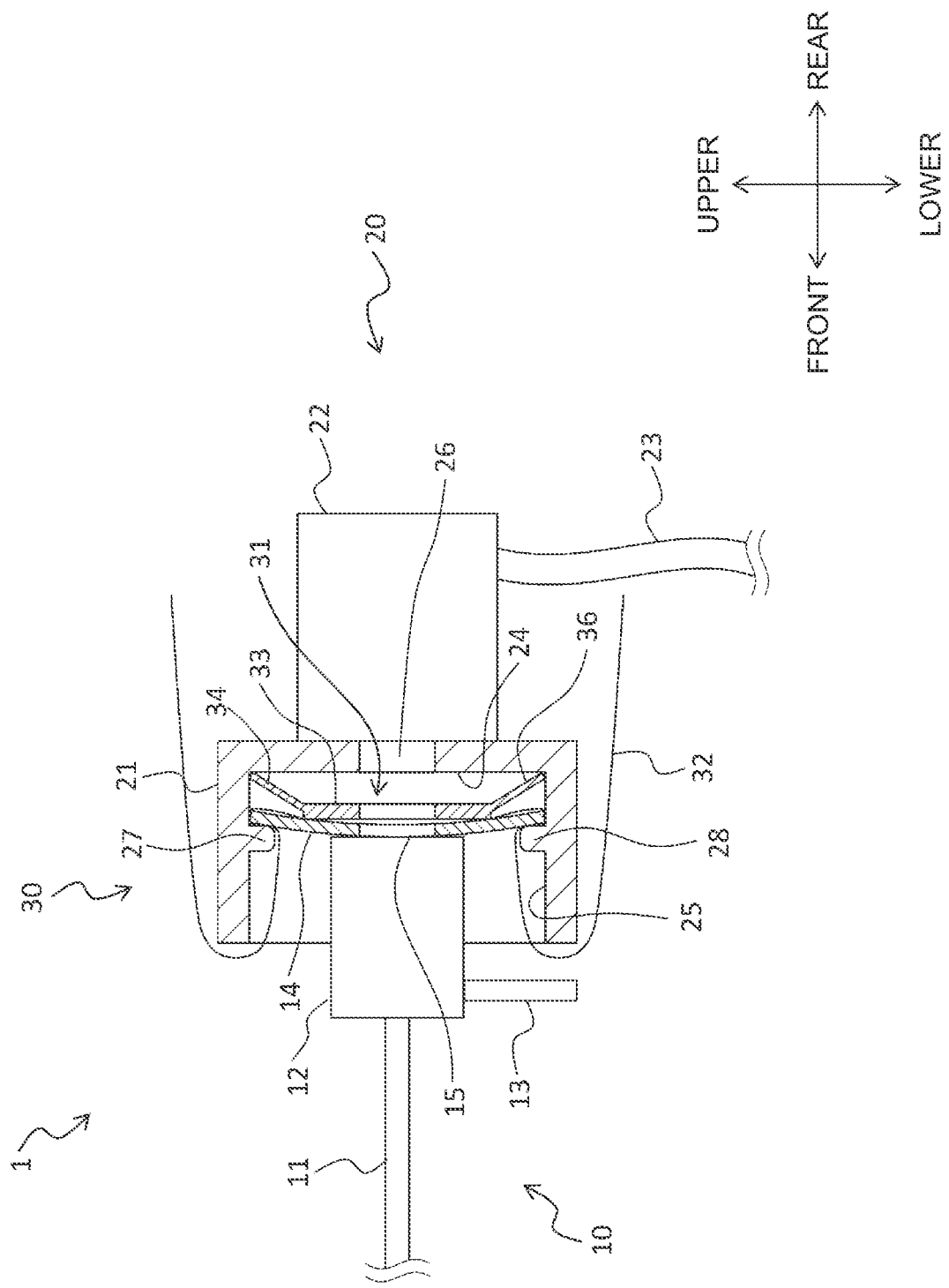

CAMERA DRAPE

This patent application is a 35 USC § 371 U.S. national stage of International Application No. PCT/JP2021/521866 filed on Apr. 20, 2021.

TECHNICAL FIELD

The present invention relates to a camera drape for use to cover a camera head to and from which a rigid endoscope is attached and detached.

BACKGROUND ART

Conventionally, in departments of digestive surgery, thoracic surgery, spinal cord surgery, otorhinolaryngology, gynecology, urology, etc., by inserting a rigid endoscope into a body, a lumen, or a body cavity, (hereinafter, referred to as an "observation object"), video has been provided for observation, diagnosis, capturing an image, or treatment of an observation object (for example, see Patent Literature 1).

A rigid endoscope has heat resistance and pressure resistance, and thus can be sterilized by high-pressure steam. On the other hand, since a camera system used to observe a surgical field is a precision instrument, there are few models of rigid endoscopes adaptable to high-pressure steam sterilization. Accordingly, aseptic surgical operations have been performed by means of covering a camera head and a camera cable with a sterilized camera drape in order to keep the rigid endoscope clean.

CITATION LIST

Patent Literature

Patent Literature 1: JP-A-2020-151403

SUMMARY OF INVENTION

Technical Problem

There are some types of camera drapes, namely, a type for covering both a rigid endoscope and a camera head and a type for selectively covering only the camera head. The type of a camera drape for covering both the rigid endoscope and the camera head has a problem that it is difficult to replace the rigid endoscope during a surgical operation.

On the other hand, the type of a camera drape for selectively covering only the camera head also has a problem that, since the camera drape typically includes a joint interposed between the rigid endoscope and the camera head, an optical distance between the rigid endoscope and the camera head is long, which results in deterioration in the quality of the video.

The present invention has been made to solve the problems above of the prior art, and an object of the present invention is to provide a camera drape which enables easy replacement of a rigid endoscope during a surgical operation while suppressing deterioration in the quality of the video.

Solution to Problem

In order to solve the problems above, the present invention provides a camera drape that covers a camera head to and from which a rigid endoscope is attached and detached, comprising: a spacer that is arranged between an endoscope-side lens of the rigid endoscope and a camera-side lens of the camera head; and a drape body that is attached to the spacer and covers, among the rigid endoscope and the camera head, only the camera head, wherein the spacer includes a clamping plate having a through hole that faces the endoscope-side lens and the camera-side lens in a state where the spacer is clamped between an eyepiece unit for supporting the endoscope-side lens and an endoscope connection unit for supporting the camera-side lens.

Advantageous Effects of Invention

According to the present invention, it is possible to obtain a camera drape which enables easy replacement of a rigid endoscope during a surgical operation while suppressing deterioration in the quality of video.

BRIEF DESCRIPTION OF DRAWINGS

FIG. 3 is an exploded cross-sectional view of the rigid endoscope system according to the present embodiment.

FIG. 4 is an assembled cross-sectional view of the rigid endoscope system according to the present embodiment.

DESCRIPTION OF EMBODIMENTS

Hereinafter, a rigid endoscope system 1 according to the present embodiment will be described with reference to the drawings. It should be noted that the embodiment described below of the present invention shows an example in which the present invention is embodied, but does not limit the scope of the present invention to the scope of the description of the embodiment. Accordingly, the present invention may be implemented by addition of various modifications to the embodiment.

The rigid endoscopy system 1 of the present embodiment is used, for example, in departments of digestive surgery, thoracic surgery, spinal cord surgery, otorhinolaryngology, gynecology, urology, for observation, diagnosis, capturing an image, or treatment of the observation object. More specifically, the rigid endoscope system 1 is configured to irradiate the observation object with irradiation light, receive the irradiation light that has been reflected by the observation object (hereinafter, referred to as "reflection light"), and photoelectrically convert the received reflection light to generate video data.

Figure 1:
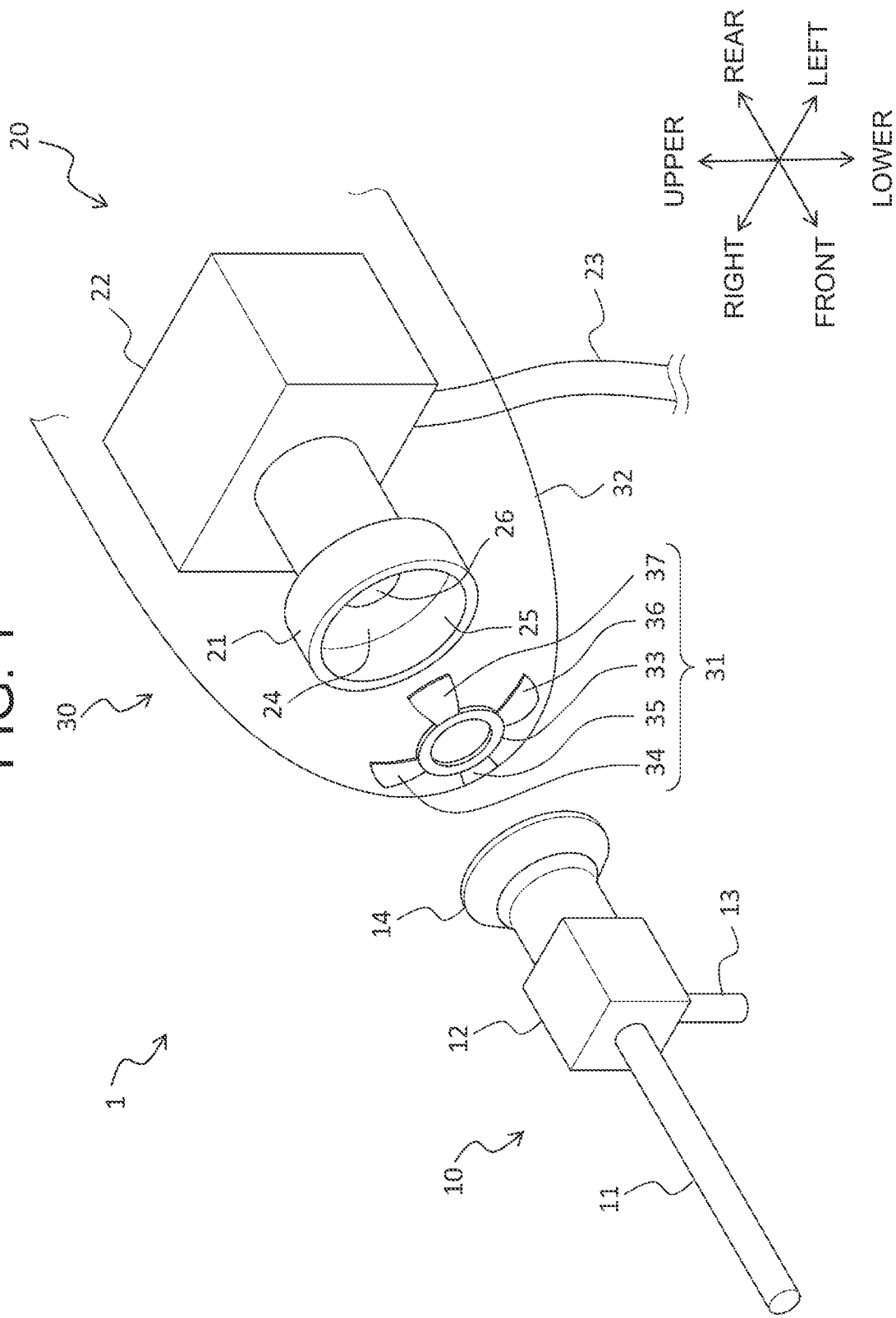
FIG. 1 is an exploded perspective view of a rigid endoscope system according to the present embodiment.

FIG. 1 is an exploded perspective view of the rigid endoscope system 1 according to the present embodiment.

Figure 2:
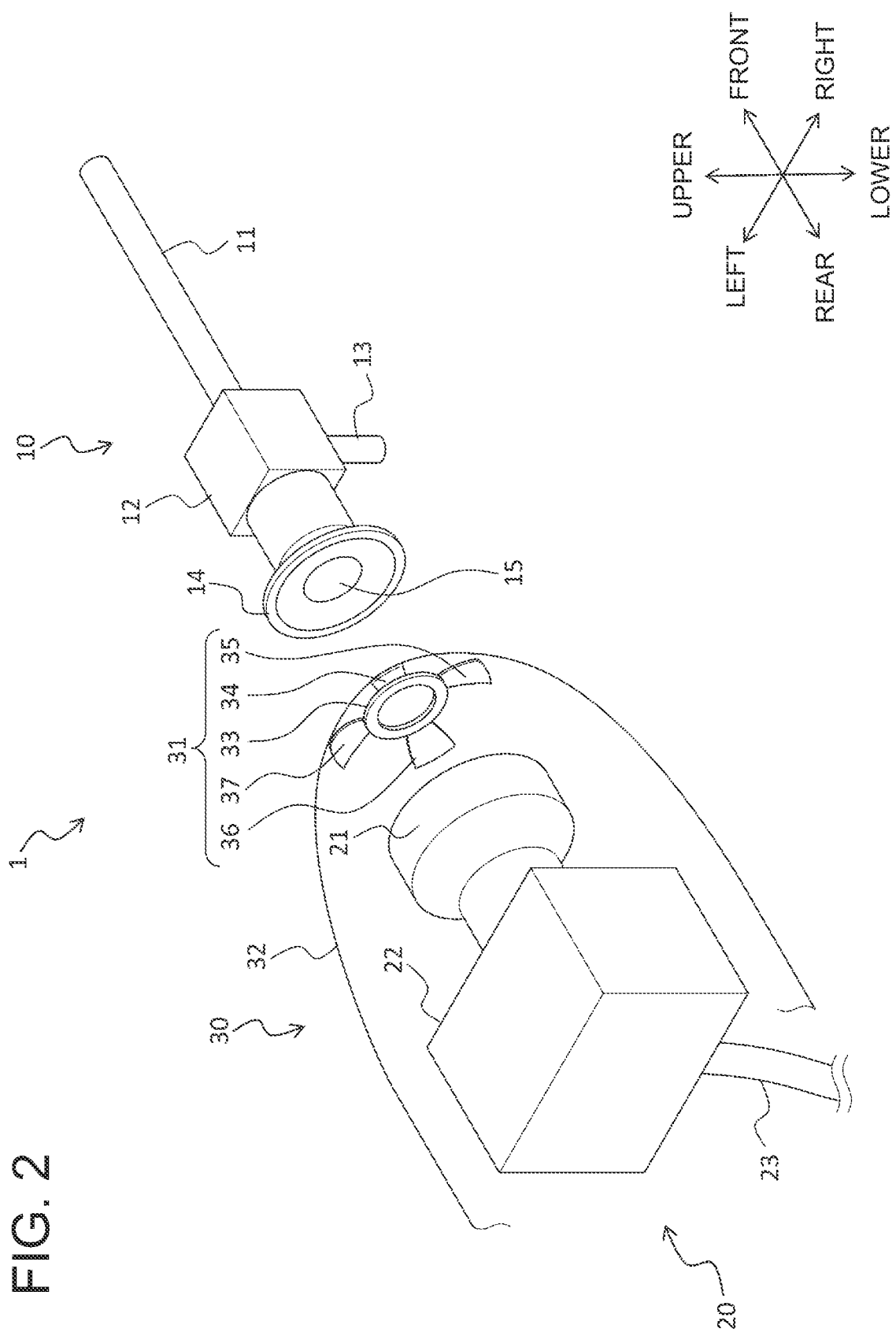
FIG. 2 is an assembled perspective view of the rigid endoscope system according to the present embodiment.

FIG. 2 is an assembled perspective view of the rigid endoscope system 1 according to the present embodiment.

FIG. 3 is an exploded cross-sectional view of the rigid endoscope system 1 according to the present embodiment.

FIG. 4 is an assembled cross-sectional view of the rigid endoscope system 1 according to the present embodiment. As illustrated in FIG. 1 to FIG. 4, the rigid endoscope system 1 mainly includes a rigid endoscope 10, a camera head 20, and a camera drape 30.

The rigid endoscope 10 is a portion that is inserted into the body, irradiates an observation object with irradiation light, and receives reflection light. The rigid endoscope 10 includes, for example, an insertion unit 11, a main body unit 12, a light input unit 13, and an eyepiece unit 14.

The insertion unit 11 is a hollow tube (for example, stainless steel tube) that extends straight. The distal end of the insertion unit 11 is to be inserted into the body. The insertion unit 11 is provided with an optical system (lens, mirror, etc.) in the inside thereof. The optical system of the insertion unit 11 irradiates the irradiation light, which has been input through the main body unit 12, from the distal end thereof to a base end thereof, and then outputs the reflection light, which has been input to the distal end thereof, from the base end thereof to the main body unit 12.

The rigid endoscope system 1 is provided with a plurality of rigid endoscopes 10 to be used selectively in accordance with a position of the observation object. In each of the plurality of rigid endoscopes 10, the optical system in the insertion unit 11 is laid out so as to output the irradiation light to different directions with respect to the extending direction of the insertion unit 11 (for example, 0°, 12°, 70°) and receive the reflection light from different directions.

The main body unit 12 is connected to the insertion unit 11, the light input unit 13, and the eyepiece unit 14. The main body unit 12 accommodates an optical system including such as a mirror and a lens. The optical system accommodated in the main body unit 12 guides the irradiation light, which has been input through the light input unit 13, to the insertion unit 11, and then guides the reflection light, which has been output from the insertion unit 11, to the eyepiece unit 14.

The light input unit 13 is a connector to and from which a light guide (optical cable) extending from a light source device (not illustrated) is attached and detached. The light input unit 13 outputs the irradiation light, which has been supplied from the light source device through the light guide, to the main body unit 12.

The eyepiece unit 14 is a portion to be attached to and detached from the camera head 20. The eyepiece unit 14 has a disk shape. More specifically, the diameter of the eyepiece unit 14 is slightly smaller than the inner diameter dimension of an endoscope connection unit 21 of the camera head 20. As illustrated in FIG. 2, the eyepiece unit 14 is provided with an endoscope-side lens 15 on the center portion thereof. The eyepiece unit 14 outputs the reflection light, which has been input from the main body unit 12, to the camera head 20 through the endoscope-side lens 15.

The camera head 20 photoelectrically converts the reflection light, which has been input from the rigid endoscope 10, to generate video data, and outputs the generated video data to a display (not illustrated), etc. The camera head 20 includes, for example, the endoscope connection unit 21, a main body unit 22, and a transfer cable 23.

The endoscope connection unit 21 is a connector to and from which the rigid endoscope 10 is attached and detached. The endoscope connection unit 21 has a bottomed cylindrical shape whose distal end is opened. The inside of the endoscope connection unit 21 is formed with a bottom wall 24 provided on a deeper side of the endoscope connection unit 21 and a cylindrical inner wall 25. The bottom wall 24 is provided with a camera-side lens 26 on the center portion thereof.

As illustrated in FIG. 3 and FIG. 4, the endoscope connection unit 21 is provided with a plurality of protrusions 27, 28 protruding inwardly from the inner wall 25. The plurality of protrusions 27, 28 protrudes and retracts from the inner wall 25 in accordance with an operation of a manipulation unit (not illustrated) manipulated by an operator. The inner diameter dimension of the inner wall 25 is slightly larger than the diameter of the eyepiece unit 14. On the other hand, the diameter of an imaginary circle connecting distal ends of the plurality of protrusions 27, 28 protruding from the inner wall 25 (hereinafter, referred to as "diameter of the inscribed circle of the plurality of protrusions 27, 28") is smaller than the diameter of the eyepiece unit 14.

The eyepiece unit 14 can be inserted into and removed from the endoscope connection unit 21 from the distal end side of the endoscope connection unit 21. When the eyepiece unit 14 inserted into the endoscope connection unit 21 gets over the plurality of protrusions 27, 28, the rigid endoscope 10 and the camera head 20 becomes connected to each other. In the connected state above, the endoscope-side lens 15 and the camera-side lens 26 face each other. As a result, the main body unit 22 receives the reflection light, which has been output from the endoscope-side lens 15, through the camera-side lens 26. On the other hand, when the manipulation unit is manipulated to make the plurality of protrusions 27, 28 retract in the inner wall 25, the connection between the rigid endoscope 10 and the camera head 20 can be released.

The main body unit 22 is connected to the endoscope connection unit 21 and the transfer cable 23, and accommodates a photoelectric conversion element (CCD, CMOS). The main body unit 22 makes use of the photoelectric conversion element to photoelectrically convert the reflection light which has been input through the camera-side lens 26 so as to generate video data, and outputs the generated video data to the transfer cable 23. In this way, video represented by the video data is displayed on the display connected to the other end of the transfer cable 23.

The rigid endoscope 10 is made of a material having heat resistance and pressure resistance, and thus can be sterilized by high-pressure steam (autoclaving). On the other hand, the camera head 20 is not adaptable to high-pressure steam sterilization since it is equipped with a precision instrument such as the photoelectric conversion element. Accordingly, in order to perform a surgical operation aseptically, it is necessary to cover the camera head 20 with the camera drape 30.

The camera drape 30 covers the camera head 20 to keep the rigid endoscope system 1 sterile in an operation room. The camera drape 30 is disposed after being used at every operation. Accordingly, it is desirable that the camera drape 30 has a simple configuration and can be easily attached and detached. The camera drape 30 includes, for example, a spacer 31 and a drape body 32.

The spacer 31 is a member interposed between the rigid endoscope 10 and the camera head 20. More specifically, the spacer 31 is arranged between the eyepiece unit 14 and the endoscope connection unit 21 so as not to make the rigid endoscope 10 contact with the camera head 20 and so as not to be interposed between the endoscope-side lens 15 and the camera-side lens 26. The spacer 31 is made of a resin material such as polyethylene terephthalate (PET) or polystyrene (PS). The spacer 31 includes, for example, a clamping plate 33 and a plurality of legs 34, 35, 36, 37. The clamping plate 33 and the plurality of legs 34 to 37 may be integrally formed, or separately formed and then assembled.

The clamping plate 33 is a plate member that is provided with a through hole on the center thereof. The clamping plate 33 has a small thickness (for example, about 0.1 mm to 2.0 mm). The outer shape of the clamping plate 33 may be a true circle, a square, a hexagon, an octagon, or the like. In the present embodiment, an example of the clamping plate 33 having a true circle shape (ring shape) will be described in detail. The outer dimension of the clamping plate 33 is smaller than the inner diameter dimension of the inner wall 25 while being larger than the diameter of the inscribed circle of the plurality of protrusions 27, 28. The inner diameter dimension of the clamping plate 33 (diameter of the through hole) is set to be equal to or larger than the diameter of the endoscope-side lens 15 and that of the camera-side lens 26.

The plurality of legs 34 to 37 is provided on the outer edge of the clamping plate 33, with being spaced apart therebetween in the circumferential direction of the clamping plate 33. More particularly, the plurality of legs 34 to 37 is equally spaced in the circumferential direction of the clamping plate 33. In the present embodiment, an example in which the four legs 34 to 37 are arranged at intervals of 90° is described, meanwhile, the number of legs is not limited to four. For example, three legs may be arranged at intervals of 120°.

Each of the plurality of legs 34 to 37 protrudes outwardly (outwardly in the radial direction) from the outer edge of the clamping plate 33. Furthermore, each of the plurality of legs 34 to 37 is bent toward one side (rear side in FIG. 1 to FIG. 4) of the thickness direction of the clamping plate 33. In the natural state, each angle formed by the plurality of legs 34 to 37 with respect to a surface of the clamping plate 33 (hereinafter, referred to as "bending angle") is set to be, for example, about 10° to 45°. Each of the plurality of legs 34 to 37 is formed to be elastically deformable toward the other side (mainly, in the direction for reducing the bending angle) of the thickness direction of the clamping plate 33.

In the natural state, the diameter of an imaginary circle connecting the distal ends of the plurality of legs 34 to 37 (end portions opposite to the other end portions connected to the clamping plate 33) is smaller than the inner diameter dimension of the inner wall 25 while being larger than the diameter of the inscribed circle of the plurality of protrusions 27, 28. When the plurality of legs 34 to 37 is elastically deformed in the direction for reducing the bending angles, the diameter of the imaginary circle connecting the distal ends of the plurality of legs 34 to 37 coincides with (that is, is expanded) the inner diameter dimension of the inner wall 25.

The drape body 32 is a film-like covering member having a size sufficient to cover the camera head 20. More particularly, among the rigid endoscope 10 and the camera head 20, the drape body 32 selectively covers only the camera head 20. The drape body 32 may be made of polyethylene which is a material generally used for a drape, whereas it may be made of a stretchable material (for example, latex or polyurethane).

The drape body 32 includes a through hole that is formed to be smaller than the outer dimension of the clamping plate 33 while being equal to or larger than the inner diameter dimension of the clamping plate 33. The drape body 32 is attached (welded) to the spacer 31 in a state where the through hole of the drape body 32 faces the through hole of the clamping plate 33. More specifically, the spacer 31 is attached to an inner surface side of the drape body 32. Here, the inner surface of the drape body 32 corresponds to the surface facing the camera head 20 in a state where the camera head 20 is covered with the drape body 32.

Next, a procedure for covering the camera head 20 with the camera drape 30 will be described. Firstly, an operator puts the drape body 32 on the camera head 20 in a state where the spacer 31 faces the distal end of the endoscope connection unit 21, whereby the whole of the endoscope connection unit 21, the main body unit 22, and the transfer cable 23 are covered with the sterilized drape main body 32 whereas the rigid endoscope 10 stays outside the drape main body 32.

Next, the operator inserts the spacer 31, which is in a state where the plurality of legs 34 to 37 faces the bottom wall 24, into the endoscope connection unit 21 from an opening at the distal end of the endoscope connection unit 21 to a position where the spacer 31 gets over the plurality of protrusions 27, 28. Then, the operator inserts the eyepiece unit 14 of the rigid endoscope 10 into the endoscope connection unit 21 to a position where the eyepiece unit 14 gets over the plurality of protrusions 27, 28 so that the through hole of the endoscope-side lens 15 faces that of the clamping plate 33.

In this way, as illustrated in FIG. 4, the drape body 32 enters the inside of the endoscope connection unit 21 along the inner wall 25, and the spacer 31 is positioned between the bottom wall 24 and the plurality of protrusions 27, 28. Furthermore, the spacer 31 is positioned between the bottom wall 24 and the eyepiece unit 14 in the inside of the endoscope connection unit 21. Still further, the drape body 32 passes through between the inner wall 25 and the outer edge of the eyepiece unit 14.

At this time, in the spacer 31, the clamping plate 33 is pressed (clamped) against the bottom wall 24 by the eyepiece unit 14, whereby the plurality of legs 34 to 37 is elastically deformed in the direction for reducing the bending angles, and the distal ends of the plurality of legs 34 to 37 are pressed against corner portions of the bottom wall 24 and the inner wall 25. As a result, the rigid endoscope 10 is stably fixed to the camera head 20 while the spacer 31 and the drape body 32 are interposed between the eyepiece unit 14 and the bottom wall 24. Furthermore, the thickness of the entire spacer 31 (that is, the distance in the front and rear direction from the front surface of the clamping plate 33 to the distal ends of the legs 34 to 37) becomes smaller than that in the natural state.

The endoscope-side lens 15 and the camera-side lens 26 face each other in a state where the through hole of the clamping plate 33 is interposed therebetween. That is, there is no component of the camera drape 30 between the endoscope-side lens 15 and the camera-side lens 26. In other words, the camera drape 30 attached to the camera head 20 does not interfere with the optical path of the reflection light between the endoscope-side lens 15 and the camera-side lens 26.

According to the embodiment above, for example, the following effects can be obtained.

According to the embodiment above, the camera head 20 is covered with the drape body 32 whereas the rigid endoscope 10 is positioned outside the drape body 32. Accordingly, the operator can replace the rigid endoscope 10 without removing the camera drape 30, thereby enabling easy replacement of the rigid endoscope 10 during a surgical operation.

Furthermore, according to the embodiment above, only the thin plate-shaped spacer 31 is interposed between the eyepiece unit 14 and the bottom wall 24 of the endoscope connection unit 21. Accordingly, the optical distance between the endoscope-side lens 15 and the camera-side lens 26 can be shortened, thereby enabling suppression of deterioration in the quality of the video provided by the rigid endoscope system 1.

Still further, according to the embodiment above, the camera drape 30 does not support the rigid endoscope 10 and the camera head 20. The spacer 31 is clamped between the eyepiece unit 14 and the endoscope connection unit 21, whereby the camera drape 30 is attached to the rigid endoscope system 1. Accordingly, the spacer 31 does not need to have high rigidity, and thus the thickness of the spacer 31 can be made small.

Still further, according to the embodiment above, since the camera drape 30 is not interposed between the endoscope-side lens 15 and the camera-side lens 26, it is possible to appropriately cover the camera head 20 while suppressing deterioration in the quality of the video obtained by the rigid endoscope 10. In addition, since the spacer 31 is accommodated in the endoscope connection unit 21, it does not interfere with the operator during a surgical operation. In this connection, note that a lens or the like may be attached to the through hole of the clamping plate 33.

Still further, according to the embodiment above, the clamping plate 33 is interposed between the eyepiece unit 14 and the bottom wall 24, and the drape body 32 is interposed between the outer edge of the eyepiece unit 14 and the inner wall 25. The rigid endoscope 10 and the camera head 20 are connected to each other in a non-contact manner, and a result, even in the case of performing a surgical operation while replacing the plurality of rigid endoscopes 10, it is possible to prevent direct contact of the rigid endoscope 10 with the camera head 20 which may be unsanitary.

Still further, according to the embodiment above, since the plurality of legs 34 to 37 is pressed against the corner portions of the bottom wall 24 and the inner wall 25, the rigid endoscope 10 can be stably supported with respect to the camera head 20. In addition, since the plurality of legs 34 to 37 is arranged at equal intervals in the circumferential direction of the clamping plate 33, a state of the rigid endoscope 10 supported by the camera head 20 is further stabilized. Meanwhile, the spacer 31 may not have the plurality of legs 34 to 37. In this case, it is desirable to set the outer dimension of the clamping plate 33 to be slightly smaller than the inner diameter dimension of the inner wall 25.

Still further, in the case of forming the drape body 32 with a stretchable material (for example, latex or polyurethane) and covering the camera head 20 therewith while expanding a portion positioned outside the endoscope connection unit 21, it is possible to prevent the drape body 32 covering a small diameter portion such as the transfer cable 23 from being bulky. Meanwhile, the drape body 32 may be made of a general material for the camera drape 30 (for example, polyethylene).

REFERENCE SIGNS LIST

1 . . . rigid endoscope system, 10 . . . rigid endoscope, 11 . . . insertion unit, 12, 22 . . . main body unit, 13 . . . light input unit, 14 . . . eyepiece unit, 15 . . . endoscope-side lens, 20 . . . camera head, 21 . . . endoscope connection unit, 23 . . . transfer cable, 24 . . . bottom wall, 25 . . . inner wall, 26 . . . camera-side lens, 27, 28 . . . protrusion, 30 . . . camera drape, 31 . . . spacer, 32 . . . drape body, 33 . . . clamping plate, 34, 35, 36, 37 . . . leg

The invention claimed is:

1. A camera drape that covers a camera head to and from which a rigid endoscope is attached and detached, comprising:
   a spacer that is arranged between an endoscope-side lens of the rigid endoscope and a camera-side lens of the camera head; and
   a drape body that is attached to the spacer and covers, among the rigid endoscope and the camera head, only the camera head, wherein the spacer includes
      a clamping plate having a through hole that faces the endoscope-side lens and the camera-side lens in a state where the spacer is clamped between an eyepiece unit for supporting the endoscope-side lens and an endoscope connection unit for supporting the camera-side lens, and
      a plurality of legs that protrudes outwardly from a plurality of positions spaced apart therebetween in a circumferential direction of the clamping plate, each of the plurality of legs being bent in an axial direction inward toward the camera head of the clamping plate, and each of the plurality of legs being elastically deformable.

2. The camera drape according to claim 1, wherein when the clamping plate is clamped between the eyepiece unit and the endoscope connection unit, the plurality of legs is are elastically deformed in the direction for reducing each bending angle so as to be pressed against corner portions of a bottom wall and an inner wall of the endoscope connection unit, the endoscope connection unit having a bottomed cylindrical shape.

3. The camera drape according to claim 1, wherein the spacer is attached to an inner surface side of the drape body which faces the camera head in a state where the camera head is covered with the drape body.

4. The camera drape according to claim 1, wherein a lens is attached to the through hole.

* * * * *